(12) United States Patent
Xia et al.

(10) Patent No.: US 9,375,401 B2
(45) Date of Patent: Jun. 28, 2016

(54) OPHTHALMIC COMPOSITIONS WITH ALKOXYLATED NATURAL WAXES

(71) Applicant: Bausch & Lomb Incorporated, Rochester, NY (US)

(72) Inventors: Erning Xia, Penfield, NY (US); Krista Fridman, Penfield, NY (US)

(73) Assignee: Bausch ÷ Lomb Incorporated, Rochester, NY (US)

( * ) Notice: Subject to any disclaimer, the term of this patent is extended or adjusted under 35 U.S.C. 154(b) by 91 days.

(21) Appl. No.: 14/377,460

(22) PCT Filed: Jan. 10, 2013

(86) PCT No.: PCT/US2013/020998
§ 371 (c)(1),
(2) Date: Aug. 7, 2014

(87) PCT Pub. No.: WO2013/126155
PCT Pub. Date: Aug. 29, 2013

(65) Prior Publication Data
US 2015/0297511 A1    Oct. 22, 2015

Related U.S. Application Data

(60) Provisional application No. 61/602,764, filed on Feb. 24, 2012.

(51) Int. Cl.

| | | |
|---|---|---|
| A61K 36/00 | (2006.01) | |
| A61K 9/00 | (2006.01) | |
| A61K 47/34 | (2006.01) | |
| A61K 9/08 | (2006.01) | |
| A61K 47/44 | (2006.01) | |
| C11D 1/66 | (2006.01) | |
| C11D 1/74 | (2006.01) | |
| C11D 3/00 | (2006.01) | |
| C11D 3/48 | (2006.01) | |
| A61L 12/14 | (2006.01) | |
| A61K 31/56 | (2006.01) | |
| A61K 31/728 | (2006.01) | |
| A61K 36/36 | (2006.01) | |
| A61K 47/36 | (2006.01) | |

(52) U.S. Cl.
CPC .......... *A61K 9/0048* (2013.01); *A61K 9/08* (2013.01); *A61K 31/56* (2013.01); *A61K 31/728* (2013.01); *A61K 36/36* (2013.01); *A61K 47/34* (2013.01); *A61K 47/36* (2013.01); *A61K 47/44* (2013.01); *A61L 12/142* (2013.01); *C11D 1/667* (2013.01); *C11D 1/74* (2013.01); *C11D 3/0078* (2013.01); *C11D 3/48* (2013.01)

(58) Field of Classification Search
None
See application file for complete search history.

(56) References Cited

U.S. PATENT DOCUMENTS

| 3,374,144 A | 3/1968 | Morris |
| 4,409,205 A | 10/1983 | Shively |
| 4,758,595 A | 7/1988 | Ogunbiyi et al. |
| 5,209,927 A | 5/1993 | Gressel et al. |
| 5,294,607 A | 3/1994 | Glonek et al. |
| 6,695,123 B2 | 2/2004 | Stoll |
| 2012/0083467 A1* | 4/2012 | Ayala et al. ............... 514/58 |

FOREIGN PATENT DOCUMENTS

| CN | 101185650 A | 5/2008 |
| JP | 04-077434 | 3/1992 |
| JP | 2000109892 A | 4/2000 |
| JP | 2002-308775 A | 10/2002 |
| JP | 2003-81840 A | 3/2003 |
| JP | 2004238346 A | 8/2004 |
| JP | 2011-517660 A | 6/2011 |
| WO | 2004/062660 A1 | 7/2004 |
| WO | 2006/079830 A1 | 8/2006 |
| WO | 2009/097028 A1 | 8/2009 |

OTHER PUBLICATIONS

Australian Patent Office Patent Examination Report No. 1 dated Jun. 17, 2015 (5 pages).
Petricek et al: "Hydroxypropyl-guar gellable lubricant eye drops for dry eye treatment" Expert Opinion on Pharmacotherpy, 2008, vol. 9(8), pp. 1431-1436.
Troiano et al: "Effect of Hypotonic 0.4% Hyaluronic Acid Drops in Dry Eye Patients: A Cross-Over Study" Cornea, vol. 27, Issue 10, p. 126-1130. 2008.
Japanese Office Action in corresponding Japanese Application No. 2014-558739 (dated Sep. 8, 2015) English translation provided by Representative Patent Attorney (7 pages).
Chinese Office Action in corresponding Chinese Application No. 201380010561.3 (dated Oct. 21, 2015) English translation provided by Representative Patent Attorney (11 pages).
International Search Report and Written Opinion of the International Searching Authority in corresponding International Application PCT/US2013/020998, completed Apr. 8, 2013 (12 pages).

* cited by examiner

*Primary Examiner* — Qiuwen Mi
(74) *Attorney, Agent, or Firm* — Toan P. Vo

(57) ABSTRACT

Ophthalmic compositions comprising 0.005 wt. % to 2.0 wt. % of alkoxylated natural waxes selected from the group consisting of alkoxylated lanolin and alkoxylated jojoba, and a method of treating a patient diagnosed with dry eye syndrome, or for cleaning and disinfecting contact lenses, with the ophthalmic compositions.

20 Claims, No Drawings

OPHTHALMIC COMPOSITIONS WITH ALKOXYLATED NATURAL WAXES

The present invention relates to ophthalmic compositions that include alkoxylated natural waxes. The invention is also directed to the use of the ophthalmic compositions as a contact lens care solution, or as eye drops to treat ocular disorders.

BACKGROUND OF THE INVENTION

Soft disposable contact lenses are commonly sold in disposable packages. The traditional blister pack packaging for disposable lenses (monthly, bi-weekly and daily) consists of a plastic receptacle for the lens (herein after referred to as a "boat"), topped by a sealing film. The boat is filled with a suitable storage solution, preferably saline, and receives a single lens in situ. The blister pack is then autoclaved using steam and pressure to achieve sterility. In some instances, storage solution will include one or more polymers selected from the group consisting of polyvinyl alcohols and their derivatives, polysaccharides and their derivatives, and also cellulose derivatives. In addition to one or more polymers identified above, the solution can also include other components known to be present in natural tears, such as calcium, potassium and/or magnesium ions.

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort during use and at the end of the day. Accordingly, it is important to remove any debris from the lens surface for continued comfortable use with a lens care cleaning and disinfecting solution that contains one or more cleaning components. It can also be important that a lens care cleaning and disinfecting solution provide a contact lens consumer with some level of ocular comfort or hydration, particularly, those consumers diagnosed with keratoconjunctivitis sicca, a condition often referred to as dry eye syndrome.

Dry eye is a common ophthalmological disorder affecting millions of people. A patient with dry eye may experience burning, a feeling of dryness, and persistent irritation. In severe cases, dry eye can seriously impair a person's vision. Also, as people age the lacrimal glands in the eye may produce less tears, resulting in eyes that become dry, inflamed, itchy, and gritty. More than 50% of total patients visiting ophthalmic clinics report dry eye syndromes. The elderly, particularly 70 to 80% of post-menopausal women suffer from ocular discomfort due to the dry eye syndrome. Although it appears that dry eye may result from a variety of unrelated pathogenic causes, all presentations of the condition share a common feature, namely the breakdown of the precorneal tear film that results in dehydration of the exposed outer ocular surface and hence the symptoms described.

A number of approaches exist for the treatment of dry eye. One common approach has been to supplement the ocular tear film using artificial tears instilled throughout the day. Examples of the tear substitute approach include the use of buffered, isotonic saline solutions and aqueous solutions containing water-soluble polymers that render the solutions more viscous and thus less easily shed by the washing action of tear fluid. See, for example, U.S. Pat. No. 5,209,927 to Gressel et al.; U.S. Pat. No. 5,294,607 to Glonek et al.; and U.S. Pat. No. 4,409,205 to Shively.

Natural waxes are often found as trace components of triglyceride oils or can be extracted from certain botanical and animal sources. Sunflower and corn oils contain natural waxes, while jojoba, carnauba and candelillia are examples of waxes found naturally in a more pure form. Beeswax and lanolin are examples of natural waxes of insect and animal origin. These example waxes range from the liquid, unsaturated jojoba oil to the almost completely saturated sunflower wax. In order to control or modify various properties of natural oils and waxes such as water solubility, one can form alkoxylated derivatives. For example, by controlling the number of ethylene oxide (ETO) and/or propylene oxide (PO) units that one attaches to the hydroxyl function of the natural waxes various properties such as solubility and melting point can be modified. Generally, it has been found that the natural oils and waxes become more water soluble as the level of alkoxylation increases. Compounds that are ethoxylated, as well as propoxylated, become more water and alcohol soluble.

Lanolin also called Adeps Lanae, wool wax or wool grease, is a yellow waxy substance secreted by the sebaceous glands of sheep. Lanolin is also frequently, but incorrectly, referred to as Wool Fat even though it well known that lanolin is devoid of glycerides and is in fact a wax, not a fat. Like many natural products, lanolin has a complex and variable composition. For example, a typical high purity grade of lanolin is composed predominantly of long chain waxy esters (ca. 97% by weight) the remainder being lanolin alcohols, lanolin acids and lanolin hydrocarbons. Certain breeds of sheep produce large amounts of lanolin, and the extraction can be performed by squeezing the sheep's harvested wool between rollers. Lanolin's role in nature is to protect wool and skin against the ravages of climate and the environment—it also seems to play a role in integument hygiene. It is therefore not surprising that lanolin and its many derivatives are used extensively in products designed for the protection, treatment and beautification of human skin.

Jojoba is a shrub native to the Sonoran and Mojave deserts of Arizona, Calif., and Mexico. Jojoba is grown commercially for its oil, a liquid wax ester, expressed from the seed. The oil is rare in that it is an extremely long (C36-C46) straight-chain wax ester and not a triglyceride, making jojoba and its derivative jojoba esters more similar to human sebum and whale oil than to traditional vegetable oils. Jojoba oil is easily refined to be odorless, colorless and oxidatively stable, and is often used in cosmetics as a moisturizer and as a carrier oil for specialty fragrances.

SUMMARY OF THE INVENTION

The invention is directed to an ophthalmic composition comprising: 0.005 wt. % to 2.0 wt. % of alkoxylated natural waxes selected from the group consisting of alkoxylated lanolin and alkoxylated jojoba. In some select embodiments, the ophthalmic composition will also include 0.002 wt. % to 0.2 wt. % hyaluronic acid or 0.05 wt. % to 0.3 wt. % hydroxypropyl guar. The invention is also directed to a method of treating a patient diagnosed with symptoms of dry eye, the method comprising instructing a patient to self administer one or more eye drops of the ophthalmic composition.

The invention is directed to a contact lens care solution comprising: 0.005 wt. % to 2.0 wt. % of alkoxylated natural waxes selected from the group consisting of alkoxylated lanolin and alkoxylated jojoba. In some select embodiments, the contact lens care solution will also include 0.002 wt. % to 0.04 wt. % hyaluronic acid or 0.005 wt. % to 0.06 wt. % hydroxypropyl guar, and one or more antimicrobial components selected from the group consisting poly(hexamethylene biguanide), which is present from 0.5 ppm to 1.5 ppm; α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm; and alexidine, which is present from 1 ppm to 4 ppm.

DETAILED DESCRIPTION OF THE INVENTION

The term "contact lens care solution" is an aqueous-based, ophthalmically acceptable composition that can be used to clean and disinfect contact lenses, particularly contact lenses classified as silicon hydrogel lenses that are prescribed for weekly, bi-weekly or monthly use, rewet or comfort solutions for use with contact lenses, and lens packaging solutions. The term "ophthalmic composition" is an ophthalmically acceptable composition that includes contact lens care solutions as well as compositions particularly formulated to treat eye-related conditions such as dry eye, to relieve allergy-related symptoms and other eye comfort formulations.

Poly(ethoxylate) lanolin or PEG lanolin is derived from lanolin by a chemical process that adds ethoxylate linkages to the hydroxyl functionality of lanolin. PEG lanolin is a flaky wax at room temperature with a slight yellow to amber color. For example, PEG75 lanolin has polymer chains with a mean length of 75 ethylene oxide units, and the resulting compound has a weight average molecular weight (MW) of about 4000 Dalton with a lanolin ester core and a polyethylene oxide chain. PEG75 lanolin is a water-soluble derivative of lanolin as a result of ethoxylation. The surrounding polyether chain allows water molecules to assemble around the non-polar and otherwise virtually water insoluble lanolin ester core. The resulting aqueous solutions are clear with a feint yellow color that increases with concentration, and are non-ionic and compatible with most physiological electrolytes, e.g. sodium chloride. PEG75 lanolin is relatively chemically inert and stable over a wide pH range. PEG75 lanolin can be obtained from Kao Chemicals.

As an alternative to the PEG derivatives of the natural wax lanolin one can also prepare a poloxamer derivative of lanolin. The poloxamer will likely have an average molecular weight from 1000 to 5000, and are listed in a BASF Product Brochure with the prefix "L" or "P" in BASF: Performance Chemicals—Surfactants: Pluronic & Tetronic. The poloxamer linkage is conjugated to the lanolin in much the same way as the commercially available PEG lanolin.

Like PEG lanolin, poly(ethoxylate) jojoba or PEG jojoba is derived from jojoba oil by a chemical process that adds ethoxylate linkages to the hydroxyl functionality of the oil. PEG jojoba is a flaky, off-white wax at room temperature. For example, PEG150 jojoba has polymer chains with a mean length of 150 ethylene oxide units. PEG150 jojoba is a completely water-soluble derivative of jojoba oil as a result of ethoxylation. PEG150 jojoba is relatively chemically inert and stable over a wide pH range. PEG150 jojoba can be obtained from Floratech® Americas.

As an alternative to the PEG derivatives of the natural wax jojoba one can also prepare a poloxamer derivative of jojoba. The poloxamer will likely have an average molecular weight from 1000 to 5000, and are listed in a BASF Product Brochure with the prefix "L" or "P" in BASF: Performance Chemicals—Surfactants: Pluronic & Tetronic. The poloxamer linkage is conjugated to the jojoba in much the same way as the commercially available PEG jojoba.

Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

In ophthalmic compositions, typically, formulated to be dispensed directly to the eye via drops, the hyaluronic acid is present in the compositions from 0.02 wt. % to 0.2 wt. %. In contact lens cleaning and disinfecting solutions, typically, formulated to be dispensed into a contact lens case, the hyaluronic acid is present in the compositions from 0.002 wt. % to 0.02 wt. %.

Guar gum is the ground endosperm of *Cyamopisis tetragonolobus* (L.) Taub. The water soluble fraction (85%) is called "guaran" (molecular weight of 220,000), which consists of linear chains of (1-4)-β-D mannopyranosyl units with α-D-galactopyranosyl units attached by (1-6) linkages. The ratio of D-galactose to D-mannose in guaran is about 1:2. The gum is primarily used in food and personal care products for its thickening property, and it has five to eight times the thickening power of starch. Guar gum may be obtained, for example, from Rhone-Polulenc (Cranbury, N.J.). Guar gum can also be derivatized to modify its properties, for example, guar derivatives such as those containing hydroxypropyl or hydroxypropyltrimonium chloride substitutions have been commercially available for over a decade. Derivatized guar of various degree of substitution are also commercially available from Rhone-Poulenc. Hydroxypropyl guar, preferably with low molar substitution (e.g., less than 0.6), is of particular interest in the ophthalmic compositions described herein.

In ophthalmic compositions, typically, formulated to be dispensed directly to the eye via drops, the hydroxypropyl guar is present in the compositions from 0.05 wt. % to 0.3 wt. %. In contact lens cleaning and disinfecting solutions, typically, formulated to be dispensed into a contact lens case, the hydroxypropyl guar is present in the compositions from 0.005 wt. % to 0.06 wt. %.

As stated, dry eye syndrome is typically defined as an ocular condition in which patients can sense a burning, a feeling of dryness, or a persistent irritation. Many suspect that dry eye arises from tear deficiency or excessive tear evaporation that causes damage to the interpalpebral ocular surface. The tear film has a thin layer of lipid (about 70 nm thick in healthy eyes) that covers the aqueous layer. The lipid layer is believed to thicken the aqueous sub-phase, to retard evaporation, to provide a smooth optical surface for the cornea, to provide a barrier against foreign particles including microbes, and to seal the lid margins during prolonged closure. Eye drops that are formulated to stabilize the lipid layer may help relieve symptoms of dry eye syndrome.

The combination of alkoxylated natural waxes, particularly alkoxylated lanolin or alkoxylatedjojoba, with hyaluronic acid or hydroxypropyl guar can be used to stabilize the thin layer of lipid of the tear film, and consequently, minimize evaporative loss of moisture from the ocular surface. In this regard, one embodiment of the invention is directed to ophthalmic compositions that comprise 0.005 wt. % to 2.0 wt. % of alkoxylated natural waxes selected from the group consisting of alkoxylated lanolin and alkoxylated jojoba in combination with 0.002 wt. % to 0.2 wt. % hyaluronic acid or 0.05 wt. % to 0.3 wt. % hydroxypropyl guar.

Applicants and others at Bausch & Lomb have developed and tested numerous ophthalmic compositions for use as lens care solutions. Lens care solutions must satisfy a number of functional characteristics. First, the solutions must possess the cleaning ability to remove denatured tear proteins and tear lipids as well as other external contaminants. Second, the solutions must possess significant disinfecting ability against a number of different bacteria and fungal strains. Third, the solutions must remain comfortable to the contact lens patient with minimal stinging as well as provide a platform to provide additional comfort or protection to the ocular surface. Lastly, the solutions must not cause significant shrinkage or swelling of the many different contact lens materials, which in turn can lead to loss in visual acuity and unwanted or pronounced lens movement.

In addition, the stabilization or maintenance of tear film is not only important for the treatment of dry eye syndrome, but also important to improve sensations of comfort and hydration in those patients that wear contact lenses. In this regard, one embodiment of the invention is directed to a contact lens care solution that comprises 0.005 wt. % to 2.0 wt. % of alkoxylated natural waxes selected from the group consisting of alkoxylated lanolin and alkoxylated jojoba in combination with 0.002 wt. % to 0.04 wt. % hyaluronic acid or 0.005 wt. % to 0.06 wt. % hydroxypropyl guar.

A contact lens cleaning and disinfecting solution will also include one or more antimicrobial components selected from poly(hexamethylene biguanide) (PHMB or PAPB), α-[4-tris (2-hydroxyethyl)-ammonium chloride-2-butenyl]poly[1-dimethyl ammonium chloride-2-butenyl]-ω-tris(2-hydroxyethyl) ammonium chloride (polyquaternium-1), and 1,1-hexamethylene-bis[5-(2-ethylhexyl)biguanide], which is referred to in the art as "alexidine". A commercial source of PHMB can be obtained from Arch Chemicals, Inc., Norwalk, Conn. under the trademark Cosmocil™ CQ. The PHMB is present in the compositions from 0.2 ppm to 2 ppm or from 0.5 ppm to 1.5 ppm. The polyquatrnium-1 is present from 1 ppm to 10 ppm or from 1 ppm to 3 ppm. The alexidine is present in the compositions from 0.5 ppm to 5 ppm or from 0.5 ppm to 2 ppm.

It is to be understood by those in the art that the compositions can include one or more of the antimicrobial components described above. For example, in one embodiment, a contact lens care solution can include polyquaternium-1 in combination with a biguanide antimicrobial component such as poly(hexamethylene biguanide) or alexidine. The polyquaternium-1 is present in relatively low concentrations, that is, from 0.5 ppm to 3 ppm, relative to the reported concentration of polyquaternium-1 in both Opti-Free®Express and Opti-Free®Replenish. Applicants believe that the polyquaternium-1 and the biguanide, in combination, can enhance the biocidal profile of the solutions.

Polyquaternium-42 is another known antimicrobial component, and is present in the ophthalmic compositions from 5 ppm to 50 ppm. Polyquaternium-42 is often used in combination with PHMB, polyquaternium-1, or alexidine, or in combination with a stabilized from of chlorine oxide such as a metal chlorite.

The contact lens care solutions or ophthalmic compositions will likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include an effective amount of a surfactant component, a viscosity inducing or thickening component, a chelating or sequestering component, or a tonicity component. The additional component or components can be selected from materials which are known to be useful in contact lens care solutions and are included in amounts effective to provide the desired functional characteristic.

Suitable surfactants can be cationic or nonionic, and are typically present (individually or in combination) in amounts up to 2% w/v. One preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas®G 2612). Still another preferred surfactant is tyloxapol.

A particular non-ionic surfactant consisting of a poly(oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The foregoing poly(oxyethylene) poly(oxypropylene) block polymer surfactants will generally be present in a total amount from 0.0 to 2% w/v, from 0. to 1% w/v, or from 0.2 to 0.8% w/v An analogous of series of surfactants, for use in the lens care compositions, is the poloxamer series which is a poly(oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

In another embodiment, the surfactant is a an amphoteric surfactant of general formula II

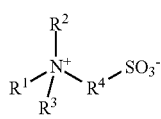

II wherein $R^1$ is R or —$(CH_2)_n$—NHC(O)R, wherein R is a $C_8$-$C_{16}$alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$alkylene optionally substituted with hydroxyl. Alternatively, one can use a hydroxysulfobetaine of general formula III

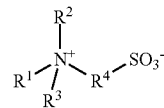

III wherein $R^1$ is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2$EDTA.

One possible alternative to the chelator $Na_2$EDTA or a possible combination with $Na_2$EDTA, is a disuccinate of formula IV below or a corresponding salt thereof;

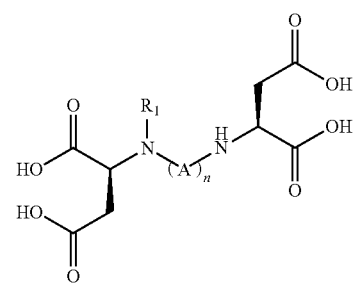

IV wherein $R_1$ is selected from hydrogen, alkyl or —C(O)alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

One exemplary contact lens care solution prepared with the components and amounts of each listed in Table 1.

TABLE 1

| Component | Minimum Amt. (wt. %) | Maximum Amt. (wt. %) | Preferred Amt. (wt. %) |
| --- | --- | --- | --- |
| boric acid | 0.10 | 1.0 | 0.64 |
| sodium borate | 0.01 | 0.20 | 0.09 |
| sodium chloride | 0.05 | 1.0 | 0.4 |
| PEG jojoba or PEG lanolin | 0.005 | 0.30 | 0.04 |
| hyaluronic acid | 0.005 | 0.04 | 0.01 |
| poloxamine or poloxamer | 0.05 | 1.0 | 0.6 |
| PHMB | 0.4 ppm | 2 ppm | 1.1 ppm |
| polyquaternium-1 | 0.5 ppm | 5 ppm | 1 ppm |

Another contact lens care solution includes the following ingredients listed in Table 2.

TABLE 2

| Component | Minimum Amt. (wt. %) | Maximum Amt. (wt. %) | Preferred Amt. (wt. %) |
| --- | --- | --- | --- |
| sorbitol or xylitol | 0.5 | 5.0 | 2.5 |
| poloxamine or poloxamer | 0.05 | 1.0 | 0.10 |
| sodium phosphate, dihydrogen | 0.10 | 0.8 | 0.46 |
| PEG jojoba or PEG lanolin | 0.005 | 0.5 | 0.10 |
| hyaluronic acid | 0.005 | 0.04 | 0.01 |
| PHMB | 0.2 ppm | 2 ppm | 1 ppm |
| Polyquaternium-1 | 1.0 ppm | 3 PPm | 1 ppm |

Other contact lens care solutions according includes the following ingredients listed in Table 3.

TABLE 3

| Component | Minimum Amt. (wt. %) | Maximum Amt. (wt. %) | Preferred Amt. (wt. %) |
| --- | --- | --- | --- |
| Tetronics ® 1304 | 0.01 | 0.2 | 0.05 |
| boric acid | 0.1 | 1.0 | 0.60 |
| sodium citrate | 0.01 | 0.4 | 0.15 |
| hydroxypropyl guar | 0.01 | 0.5 | 0.05 |
| PEG jojoba or PEG lanolin | 0.02 | 0.1 | 0.08 |
| polyquaternium-1 | 0.5 ppm | 10 ppm | 5 ppm |

As described, the ophthalmic compositions can be used to clean and disinfect contact lenses as a daily care regimen. The procedure includes removing the contact lens from the eye, adding a few drops of the solution to each side of the lens, followed by gently rubbing the surface between ones fingers for approximately 3 to 10 seconds, rinsing both sides of the lens with a few milliliters of solution and placing the lens in a lens storage case. The lens is then immersed in fresh solution for at least two hours. The lens is then removed from the case, optionally rinsed with more solution, and repositioned on the eye.

The ophthalmic compositions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

The ophthalmic compositions can also be formulated as a contact lens rewetting eye drop solution. By way of example, the rewetting drops may be formulated according to any one of the foregoing formulations of Tables 1 to 3 above. Alternatively, the formulations may be modified by increasing the amount of surfactant; by reducing the amount of antimicrobial agent to a preservative amount and/or by adding a humectant and/or demulcent.

The ophthalmic compositions can be used as a preservative in formulations for treating patients with dry eye. In such a method, the ophthalmic composition is administered to the patient's eye, eye lid or to the skin surrounding the patient's eye. The compositions can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

EXAMPLE NOS. 1 to 4

Contact lens care solutions of Example Nos. 1 to 5 of Table 4 are prepared using the following process (components are listed in wt. % unless noted in ppm). A volume of purified water equivalent to 70-90% of the total batch weight is added to a stainless steel mixing vessel. The following batch quantities of components are added to the water with stirring in the order listed: sodium chloride, edetate disodium, boric acid, sodium borate, Dequest® 2016 (if required), the PEG-75 lanolin and Tetronics® 1107. The solution is mixed (stirred) for not less than 10 minutes to ensure complete dissolution of each of the components. If sodium hyaluronate is to be added, the solution is warmed to a temperature not less than 70° C. and then the sodium hyaluronate is added. The warmed solution is stirred for at least 20 minutes until the sodium hyaluronate appears to be completely dissolved. The pH of the resulting solution is measured at room temperature, and if necessary, the pH is adjusted with 1N NaOH or 1N HCl (target pH=7.5). In a second stainless steel vessel, a measured amount a measured amount of PHMB required for the batch is added to a given amount of purified water, and the solution is stirred for at least 10 minutes. In a third stainless steel vessel, a measured amount of polyquaternium-1, if required, is added to a given amount of purified water, and the solution is stirred for at least 10 minutes. The final solution is stirred for at least 15 minutes.

TABLE 4

| | Example | | | | |
|---|---|---|---|---|---|
| | 1 | 2 | 3 | 4 | 5 |
| boric acid | 0.60 | 0.55 | 0.64 | 0.65 | 0.64 |
| sodium borate | 0.105 | 0.11 | 0.12 | 0.09 | 0.09 |
| sodium chloride | 0.50 | 0.45 | 0.50 | 0.40 | 0.5 |
| Na$_2$EDTA | 0.11 | 0.11 | 0.06 | 0.05 | 0.05 |
| Dequest ® 2016 | 0.05 | 0.1 | — | 0.1 | 0.1 |
| Tetronics ® 1107 | 0.5 | 0.5 | 0.6 | 0.5 | 0.5 |
| sodium hyaluronate | 0.01 | 0.01 | 0.01 | — | — |
| PEG lanolin | 0.03 | 0.04 | 0.02 | 0.02 | 0.01 |
| PHMB (ppm) | 1.3 | 0.8 | 1.1 | 1.0 | 0.8 |
| polyquaternium-1 (ppm) | — | 1.5 | 1.0 | 1.0 | 1.0 |

Applicants tested ophthalmic solutions that contained PEG75 lanolin and one or more antimicrobial components. Contact lens solutions were prepared containing varying amounts of PEG75 lanolin and either 1.3 ppm PHMB or 3 ppm polyquaternium-1. The solution formulations also included the components of Example 4 in Table 8. In the case of the PHMB/PEG-lanolin solutions, PEG75 lanolin appears to have a slightly negative impact on the biocidal activity of the PHMB solutions against the tested organisms, Table 5. No difference in antimicrobial activity was observed in the PQ-1 solutions, Table 6.

TABLE 5

Lens care solutions with PEG lanolin and PHMB.

| Solution No. PEG-lanolin (wt. %) | S. aureus | P. aeruginosa | S. marcescens | C. albicans | F. solani |
|---|---|---|---|---|---|
| 1.3 PHMB | 4.4 | 3.8 | 3.7 | 2.4 | 2.7 |
| 1 (0.15) | 2.8 | >4.8 | 3.5 | 0.5 | 1.1 |
| 2 (0.075) | 3.0 | >4.8 | 2.6 | 0.9 | 2.2 |
| OF Replenish | 3.8 | >4.8 | 3.4 | 0.8 | 2.0 |

TABLE 6

Lens care solutions with PEG-lanolin and PQ-1.

| Solution No. PEG-lanolin (wt. %) | S. aureus | P. aeruginosa | S. marcescens | C. albicans | F. solani |
|---|---|---|---|---|---|
| 3.0 PQ-1 | 4.4 | >4.6 | >4.6 | 1.0 | 4.1 |
| 1 (0.15) | 4.3 | 4.4 | 4.6 | 1.1 | 4.3 |
| 2 (0.075) | 4.1 | >4.6 | >4.6 | 1.2 | 4.3 |
| OF Replenish | 3.7 | 4.6 | 3.2 | 0.5 | 1.8 |

Biocidal Stand-Alone Stability

In order to assess the activity of the formulation, samples of Example No. 4 were bottled in 4 oz PET containers and stored at ambient temperature, as well as elevated temperatures for a given period. The stand-alone biocidal efficacy of the samples is tested at designated intervals to determine the stability of the formulation with time for disinfection activity, see Table 7. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure.

The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using Staphylococcus aureus (ATCC 6538), Pseudomonas aeruginosa (ATCC 9027), Serratia marcescens (ATCC 13880), Candida albicans (ATCC 10231) and Fusarium solani (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. Serratia marcescens, as appropriate, is filtered through a 1.2 μm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1\times10$ to $1\times10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the specified time points.

Biocidal stand-alone stability data was obtained with Example No. 4 and is reported in Table 7. A comparison of the 40° C. data at one month with the 40° C. data at six months indicates a one-log decrease in biocidal reduction against C.

*albicans* and almost a two-log decrease in biocidal reduction against *F. soluni*, however, even the 40° C. data at six months as well as nine months passes the one-log reduction requirement for the fungi under the FDA's stand alone procedure. Interestingly, OptiFree® Replenish, a leading contact lens care solution, appears to fail the one-log reduction FDA requirement for *C. albicans* at to at 25° C. under identical testing conditions.

EXAMPLE NOS. 6 to 10

Example compositions were prepared based on the following base formulation (wt. %): 0.65 boric acid; 0.09 sodium borate; 0.4 sodium chloride; 0.05 $Na_2EDTA$; 0.1 Dequest® 2016; 0.5 poloxamine 1107; 0.02 PEG75 lanolin; and the specified concentration of PHMB and polyquaternium-1. The compositions as Q.S. to 100% water and are listed in Table 8.

TABLE 7

Four-hour biocidal stability in PET bottles at elevated temperatures.

| Time point | ° C. | Sa | Pa | Sm | Ca | Fs |
|---|---|---|---|---|---|---|
| $t_0$ | 25 | 3.3 | >4.6 | 3.6 | 2.2 | 3.9 |
| one month | 25 | >4.9 | >4.6 | >4.6 | 2.2 | 4.4 |
|  | 40 | >4.9 | >4.6 | >4.6 | 2.4 | 4.2 |
|  | 50 | >4.9 | >4.6 | >4.6 | 2.3 | 4.4 |
| two month | 25 | 4.9 | >4.6 | >4.6 | 1.9 | 3.8 |
|  | 50 | 4.1 | >4.6 | 3.3 | 1.7 | 2.7 |
| three month | 25 | >4.8 | >4.7 | 4.6 | 2.2 | 2.4 |
|  | 50 | 4.4 | >4.7 | 3.4 | 0.8 | 1.2 |
| four month | 25 | 4.7 | >4.7 | 3.2 | 1.7 | 3.0 |
|  | 40 | >4.9 | >4.7 | 3.5 | 1.7 | 3.1 |
|  | 50 | 3.8 | >4.7 | 3.3 | 0.7 | 0.8 |
| six month | 25 | >4.8 | >4.8 | 3.8 | 1.6 | 2.8 |
|  | 40 | >4.8 | >4.8 | 4.8 | 1.4 | 2.1 |
| nine month | 25 | 4.6 | >4.6 | 4.6 | 1.5 | 1.9 |
|  | 40 | 4.3 | >4.6 | 4.6 | 1.3 | 1.6 |
| $t_0$ | Opti-Free® Replenish 25° C. | 3.6 | >4.6 | 3.1 | 0.9 | 2.9 |

TABLE 8

|  | Example | | | | |
|---|---|---|---|---|---|
|  | 6 | 7 | 8 | 9 | 10 |
| PAPB (ppm) | — | 0.3 | 0.6 | 0.9 | 1.3 |
| polyquaternium-1 (ppm) | 1.0 | 1.0 | 1.0 | 1.0 | 1.0 |
| Example No. | Sa | Pa | Sm | Ca | Fs |
| 6 | 3.6 | >4.6 | 4.6 | 0.4 | 1.6 |
| 7 | 4.7 | >4.6 | 4.4 | 0.7 | 2.5 |
| 8 | 4.7 | >4.6 | 3.8 | 1.2 | 3.5 |
| 9 | >4.7 | >4.6 | >4.6 | 2.0 | 4.5 |
| 10 | >4.7 | >4.6 | 4.6 | 3.1 | 3.7 |
| OF Replenish | 3.8 | >4.6 | 3.1 | 0.7 | 3.5 |

EXAMPLE NOS. 11 to 15

A dose study was conducted for contact lens care solutions that include different concentrations of PEG-75 lanolin, and the solutions are listed in Table 9. The example compositions were prepared based on the following base formulation (wt. %): 0.65 boric acid; 0.09 sodium borate; 0.4 sodium chloride; 0.05 $Na_2EDTA$; 0.1 Dequest® 2016; 0.5 poloxamine 1107; 1.3 ppm PHMB and Q.S. to 100% water.

TABLE 9

|  | Example | | | | | |
|---|---|---|---|---|---|---|
|  | 11 | 12 | 13 | 14 | 15 | control |
| PEG-75 lanolin | 0.1 | 0.2 | 0.3 | 0.4 | 0.5 | — |
| Example No. | Sa | Pa | Sm | Ca | Fs |  |
| 11 | 3.6 | >4.5 | 3.2 | 2.4 | 3.0 |  |
| 12 | 3.4 | >4.5 | 3.3 | 2.3 | 2.5 |  |
| 13 | 3.5 | >4.5 | 3.4 | 1.8 | 2.2 |  |
| 14 | >4.7 | >4.5 | 3.4 | 1.4 | 1.9 |  |
| 15 | >4.7 | 4.5 | 3.4 | 1.2 | 1.9 |  |
| control | 4.5 | >4.5 | 3.5 | 2.7 | 3.3 |  |

Preliminary Clinical Evaluation of Example No. 4.

Twenty-one (21) subjects completed a two hour, dispensing study using PureVision® lenses from Bausch & Lomb, Inc., comparing the formulation of Example No. 4 to control solution (a marketed lens care solution with 10 ppm of polyquaternium-1 and Aldox®). Each well of the lens cases was pre-treated (a single, 4-hour minimum soak) with either test solution or control solution. For each case, the well treated with test solution was randomly determined and the other well received the control solution. All of the lenses were pre-treated (4-hour minimum soak), with either the test solution or control solution, in the pre-treated lens cases, following the same randomization used for the lens case wells.

Of the 21 subjects who completed the study, three (3) preferred the test solution and five (5) preferred the control at insertion of the lenses. Thirteen (13) stated no difference. Also, there was no statistically significant difference for mean sting/burn between the test solution and the control solution eyes for the two hour duration of the test.

PHMB Uptake Study

A PHMB uptake study was performed in two buffered borate saline (BBS) solutions; one with a total of 5.0 ppm PHMB (control), and one with a total of 5.0 ppm PHMB plus 0.02 wt. % of PEG-75 lanolin (test). The concentrations of PHMB were determined based on the absorbance of the test and control solutions at 235 nm. It was found that PureVision® lenses absorbed approximately 3.055 ppm PHMB after an overnight soak in the control solution, accounting for an approximately 62% uptake of PHMB. In contrast, PureVision® lenses absorbed approximately 1.907 ppm PHMB after an overnight soak in the test solution, accounting for approximately 38% uptake of PHMB. The difference in percent uptake of PHMB by PureVision® lenses after an overnight soak is about 39%, i.e., [62−38]/62×100. Absorbance values observed indicated that PEG-75 lanolin also absorbs at 235 nm. These values should thus be used as an indicator of what may be expected if a PHMB uptake study were conducted in the presence of PEG-75 lanolin.

Lens Compatibility Testing

TABLE 10

Lens compatibility data of commercial lenses with Example No. 4.

| Soft Contact Lens Type | Parameter | ISO Spec | 30 Cycles |
|---|---|---|---|
| ACUVUE® 2 | Diameter | ±0.20 mm | In spec |
|  | Estimated Base Curve | ±0.20 mm | In spec |
| ACUVUE® OASYS | Diameter | ±0.20 mm | In spec |
|  | Estimated Base Curve | ±0.20 mm | In spec |
| PureVision® | Diameter | ±0.20 mm | In spec |
|  | Estimated Base Curve | ±0.20 mm | In spec |

We claim:

1. An ophthalmic composition comprising 0.005 wt. % to 2.0 wt. % of alkoxylated natural waxes selected from the group consisting of alkoxylated lanolin and alkoxylated jojoba, and 0.002 wt. % to 0.2 wt. % hyaluronic acid or 0.05 wt. % to 0.3 wt. % hydroxypropyl guar, and having a pH of from 6 to 8.4.

2. The composition of claim 1 wherein the alkoxylated natural wax is alkoxylated lanolin.

3. The composition of claim 2 wherein the alkoxylated lanolin is PEG75 lanolin.

4. The composition of claim 1 wherein the alkoxylated natural wax is a poloxamer derivative of lanolin.

5. The composition of claim 1 wherein the alkoxylated natural wax is alkoxylated jojoba.

6. The composition of claim 5 wherein the alkoxylated jojoba is PEG150 jojoba.

7. The composition of claim 1 wherein the alkoxylated natural wax is a poloxamer derivative of jojoba.

8. The composition of claim 1 wherein the composition further comprises a pharmaceutical agent.

9. The composition of claim 1 wherein the composition has a pH of from 6 to 8.

10. A contact lens care solution comprising: 0.005 wt. % to 2.0 wt. % of alkoxylated natural waxes selected from the group consisting of alkoxylated lanolin and alkoxylated jojoba; 0.002 wt. % to 0.04 wt. % hyaluronic acid or 0.005 wt. % to 0.06 wt. % hydroxypropyl guar; and one or more antimicrobial components selected from the group consisting of poly(hexamethylene biguanide), which is present from 0.5 ppm to 1.5 ppm; α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm; and alexidine, which is present from 1 ppm to 4 ppm, and having a pH of from 6 to 8.4.

11. The lens care solution of claim 10 wherein the alkoxylated natural wax is alkoxylated lanolin.

12. The lens care solution of claim 10 wherein the alkoxylated natural wax is a poloxamer derivative of lanolin.

13. The lens care solution of claim 10 wherein the alkoxylated natural wax is alkoxylated jojoba.

14. The lens care solution of claim 10 wherein the alkoxylated natural wax is a poloxamer derivative of jojoba.

15. The lens care solution of claim 10 further comprising dexpanthenol, sorbitol, glycolic acid, propylene glycol, 2-amino-2-methyl-1,3-propanediol or any mixture thereof.

16. A contact lens care solution of claim 10, for sensitive eyes, the composition comprising 0.5 ppm to 1.5 ppm of poly(hexamethylene biguanide).

17. The contact lens care solution of claim 16 further comprising α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 1 ppm to 10 ppm, or alexidine, which is present from 1 ppm to 4 ppm.

18. The contact lens care solution of claim 16 wherein the alkoxylated natural wax is a poloxamer derivative of jojoba or a poloxamer derivative of lanolin.

19. The contact lens care solution of claim 10 wherein the solution has a pH of from 6 to 8.

20. A method of treating a patient diagnosed with symptoms of dry eye, the method comprising instructing a patient to self administer one or more eye drops of an ophthalmic composition comprising 0.005 wt. % to 2.0 wt. % of alkoxylated natural waxes selected from the group consisting of alkoxylated lanolin and alkoxylated jojoba, and 0.002 wt. % to 0.2 wt. % hyaluronic acid or 0.05 wt. % to 0.3 wt. % hydroxypropyl guar, and having a pH of from 6 to 8.4.

* * * * *